United States Patent [19]

Garritano

[11] Patent Number: 4,601,195

[45] Date of Patent: Jul. 22, 1986

[54] APPARATUS AND METHOD FOR MEASURING VISCOELASTIC PROPERTIES OF MATERIALS

[75] Inventor: Ronald F. Garritano, Flemington, N.J.

[73] Assignee: Rheometrics, Inc., Piscataway, N.J.

[21] Appl. No.: 722,150

[22] Filed: Apr. 11, 1985

[51] Int. Cl.[4] ............................................. G01N 11/00
[52] U.S. Cl. .......................................... 73/60; 73/843
[58] Field of Search ...................... 73/59, 60, 841, 843

[56] References Cited

U.S. PATENT DOCUMENTS

| | | | |
|---|---|---|---|
| 3,122,914 | 3/1964 | Stabe et al. | 73/59 |
| 3,465,575 | 9/1969 | Kepes | 73/60 |
| 3,545,257 | 12/1970 | Zemp et al. | 73/59 |
| 4,092,849 | 6/1978 | Maxwell | 73/843 |
| 4,173,142 | 11/1979 | Heizn | 73/60 |
| 4,302,967 | 12/1981 | Dufey | 73/843 |
| 4,375,049 | 2/1983 | Nelson et al. | 73/59 |
| 4,535,621 | 8/1985 | Gervais et al. | 73/843 |

FOREIGN PATENT DOCUMENTS

| | | | |
|---|---|---|---|
| 1365677 | 9/1974 | United Kingdom | 73/60 |
| 595657 | 2/1978 | U.S.S.R. | 73/60 |
| 613227 | 6/1978 | U.S.S.R. | 73/60 |

Primary Examiner—Stewart J. Levy
Assistant Examiner—Hezron E. Williams
Attorney, Agent, or Firm—Samuelson & Jacob

[57] ABSTRACT

Apparatus and method for measuring the viscous component and the elastic component of forces within a viscoelastic test specimen placed in shear, the test specimen being coupled to a platen having a rest position, the platen being displaceable from the rest position rotationally and axially relative to a fixed axis in response to rotational and axial forces exerted by the test specimen upon the platen as a result of the viscous component and the elastic component, the apparatus and method including an arrangement of component parts and a plurality of steps for establishing a rotational counterforce for balancing the rotational force on the platen and simultaneously establishing an axial counterforce for balancing the axial force on the platen to maintain the platen at the rest position, and indicating the magnitude of the counterforces necessary to maintain the platen at the rest position, whereby the viscous component and the elastic component of forces are measured at zero compliance.

23 Claims, 4 Drawing Figures

APPARATUS AND METHOD FOR MEASURING VISCOELASTIC PROPERTIES OF MATERIALS

The present invention relates generally to the measurement of rheological characteristics of materials and pertains, more specifically, to apparatus and method for measuring both the viscous and the elastic components of forces within a test specimen placed in shear.

In the evaluation of rheological characteristics of visoelastic materials, such as polymer melts, a disk-like specimen usually is placed between opposed, axially spaced apart, radially-extending surfaces and is coupled to each surface, filling the axial spacing between the surfaces. One of the surfaces then is rotated about the axial direction relative to the other to place the test specimen in shear and the torque resulting from the shear is measured. The shear may be steady shear, in which case the measured torque is constant, or the shear may be dynamic shear, in which case the measured torque changes continuously with time. The measured torque is proportional to the viscous, or loss component of the modulus of the material.

It has been observed that as a result of the nature of the forces applied to the test specimen in such a procedure, the test specimen has a tendency to expand axially, thereby placing axially directed forces upon the relatively rotating surfaces to which the specimen is coupled. That tendency has been explained to result from the fact that the center of the test specimen remains stationary while the outer perimeter is rotated, so that the radially outer portions of the test specimen tend to draw radially inwardly and exert axial forces upon the surfaces to which the specimen is coupled. This behavior has been referred to in the literature as the "Weissenberg Effect." The axial force exerted upon the surfaces by the test specimen under shear conditions is proportional to the elastic, or storage component of the modulus of the material.

Although apparatus and method have been available for measuring rotational and axial forces in such a test specimen, prior devices require actual displacement of component parts of these measuring devices in order to obtain a measure of the rotational and axial forces. This displacement is known as compliance and, although it is recognized that it is desirable to reduce compliance in order to retain increased accuracy, prior devices have required at least some compliance in order to operate. It would be advantageous to have available apparatus and method in which the measurement of the rotational and axial forces could be accomplished without introducing such movement, or, in other words, at zero compliance. By eliminating the necessity for compliance, or movement, forces are measured directly, thereby attaining greater accuracy since extraneous effects essentially are eliminated. For example, force measurement now becomes independent of the effects of temperature on the measuring apparatus. Further, the ability to measure force independent of displacement eliminates any effects due to hysteresis which could occur, for example, in the measurement of a force acting against a spring.

It is an object of the present invention to provide apparatus and method which enable the measurement of both the viscous and the elastic components of forces in a viscoelastic material in shear with zero compliance.

Another object of the invention is to provide apparatus and method as described above and in which both the viscous and the elastic components are measured simultaneously, with zero compliance, for increased accuracy in obtaining data pertaining to viscoelastic properties independent of extraneous effects.

Still another object of the invention is to provide apparatus as described above and in which a high degree of accuracy is attained through the use of movable components which have no preferred positions and therefore introduce no error which might otherwise occur as a result of the tendency to move toward a preferred position.

Yet another object of the invention is to provide apparatus of the type described above and which is relatively simple in construction, enabling economy of manufacture as well as ease of maintenance and use.

The above objects, as well as still further objects and advantages, are attained by the present invention which may be described briefly as apparatus for measuring the viscous component and the elastic component of forces within a viscoelastic test specimen placed in shear, the test specimen being coupled to a platen having a rest position, the platen being displaceable from the rest position rotationally and axially relative to a fixed axis in response to rotational and axial forces exerted by the test specimen upon the platen as a result of the viscous component and the elastic component, the apparatus comprising: a first transducer coupled with the platen for applying a rotational counterforce to the platen for biasing the platen toward the rest position; a first detector for detecting rotational movement of the platen away from the rest position; a first drive means for actuating the first transducer in response to the first detector to balance the rotational force exerted by the test specimen upon the platen with the rotational counterforce exerted by the first transducer upon the platen and maintain the platen at the rest position; first indicating means for indicating the magnitude of the rotational counterforce; a second transducer coupled with the platen for applying an axial counterforce to the platen for biasing the platen toward the rest position; a second detector for detecting axial movement of the platen away from the rest position; second drive means for actuating the second transducer in response to the second detector to balance the axial force exerted by the test specimen upon the platen with the axial counterforce exerted by the second transducer upon the platen and maintain the platen at the rest position; and second indicating means for indicating the magnitude of the axial counterforce; whereby the first indicating means provides a measure of the viscous component of forces within the test specimen and the second indicating means provides a measure of the elastic component of forces within the test specimen when the platen is at the rest position.

The invention may be described further as the method of measuring the viscous component and the elastic component of forces within a viscoelastic test specimen placed in shear, the test specimen being coupled to a platen having a rest position, the platen being displaceable from the rest position rotationally and axially relative to a fixed axis in response to rotational and axial forces exerted by the test specimen upon the platen as a result of the viscous component and the elastic component, the method comprising the steps of: applying a rotational counterforce to the platen for biasing the platen toward the rest position; balancing the rotational force exerted by the test specimen upon the platen with the rotational counterforce applied to the platen to maintain the platen at the rest position; determining the magnitude of the rotational counterforce necessary to balance the rotational force; applying an axial counterforce to the platen for biasing the platen toward the rest position; balancing the axial force exerted by the test specimen upon the platen with the axial counterforce applied to the platen to maintain the platen at the rest position; and determining the magnitude of the axial counterforce necessary to balance the axial force; whereby the magnitude of the rotational counterforce provides a measure of the viscous component of forces within the test specimen and the magnitude of the axial counterforce provides a measure of the elastic component of forces within the test specimen when the platen is at the rest position.

The invention will be understood more fully, while still further objects and advantages will become apparent, in the following detailed description of a preferred embodiment illustrated in the accompanying drawing, in which.

Figure 1:
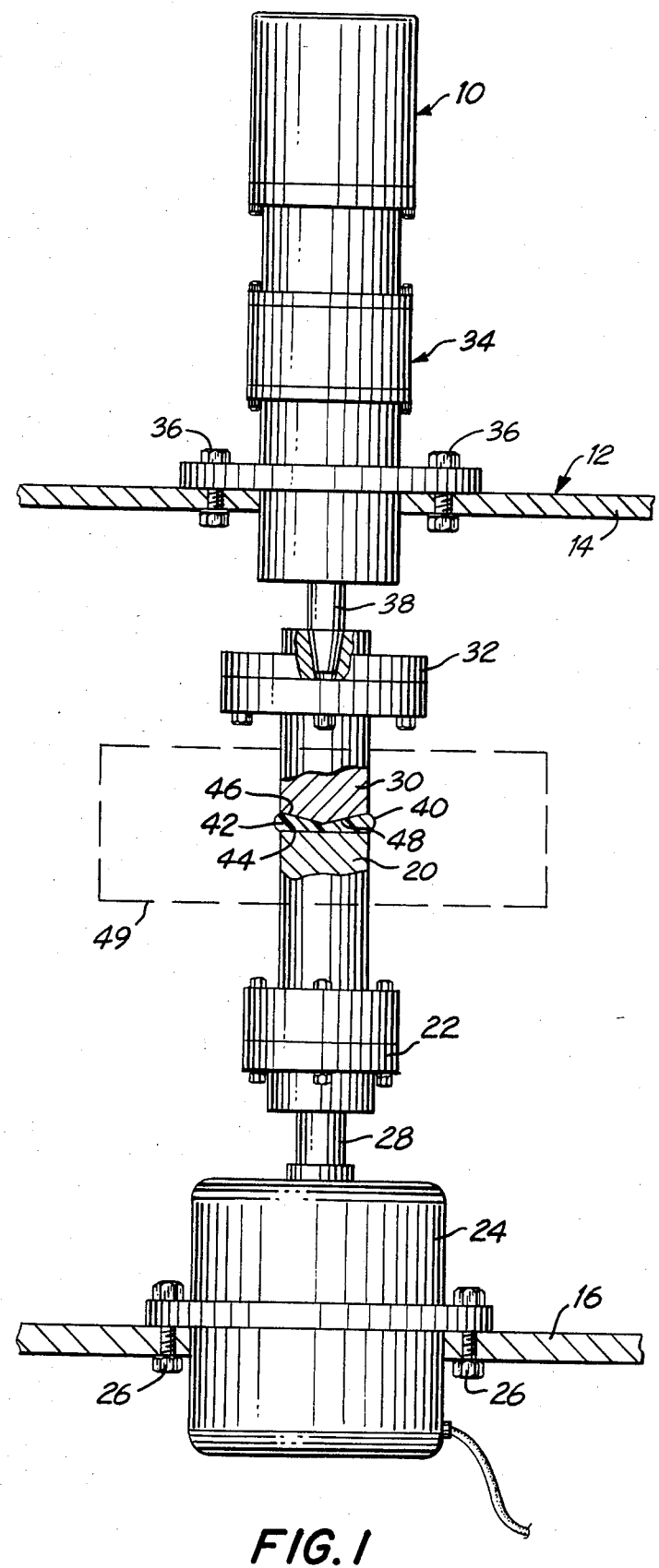
FIG. 1 is an elevational view, partially sectioned and partially diagrammatic, illustrating an apparatus constructed in accordance with the invention.

Referring now to the drawing, and especially to FIG. 1 thereof, an apparatus 10 is shown constructed in accordance with the invention. Apparatus 10 includes a frame 12 having an upper support member 14 and a lower support member 16. A table 20 is coupled, by means of a lower coupling 22, to a motor 24 mounted upon lower support member 16 by means of bolts 26. Lower coupling 22 is secured to drive shaft 28 of motor 24. A platen 30 is coupled, by means of an upper coupling 32, to a transducer assembly 34 mounted upon upper support member 14 by means of bolts 36. Upper coupling 32 is secured to spindle 38 of transducer assembly 34.

A test specimen 40 of viscoelastic material is placed between the table 20 and the platen 30 and is coupled to both the table 20 and the platen 30. In this instance, the test specimen 40 is in the form of a disk 42 of polymer melt whose viscoelastic properties are to be measured, disk 42 having a lower surface 44 fixed to table 20 and an upper surface 46 fixed to platen 30. As is usual in devices in which such measurements are performed, platen 30 is provided with a generally conical surface 48 to which upper surface 46 of disk 42 is fixed. Since, in this instance, test specimen 40 is a polymer melt, an oven 49 is provided to maintain the test specimen 40 at a desired elevated temperature.

Figure 2:
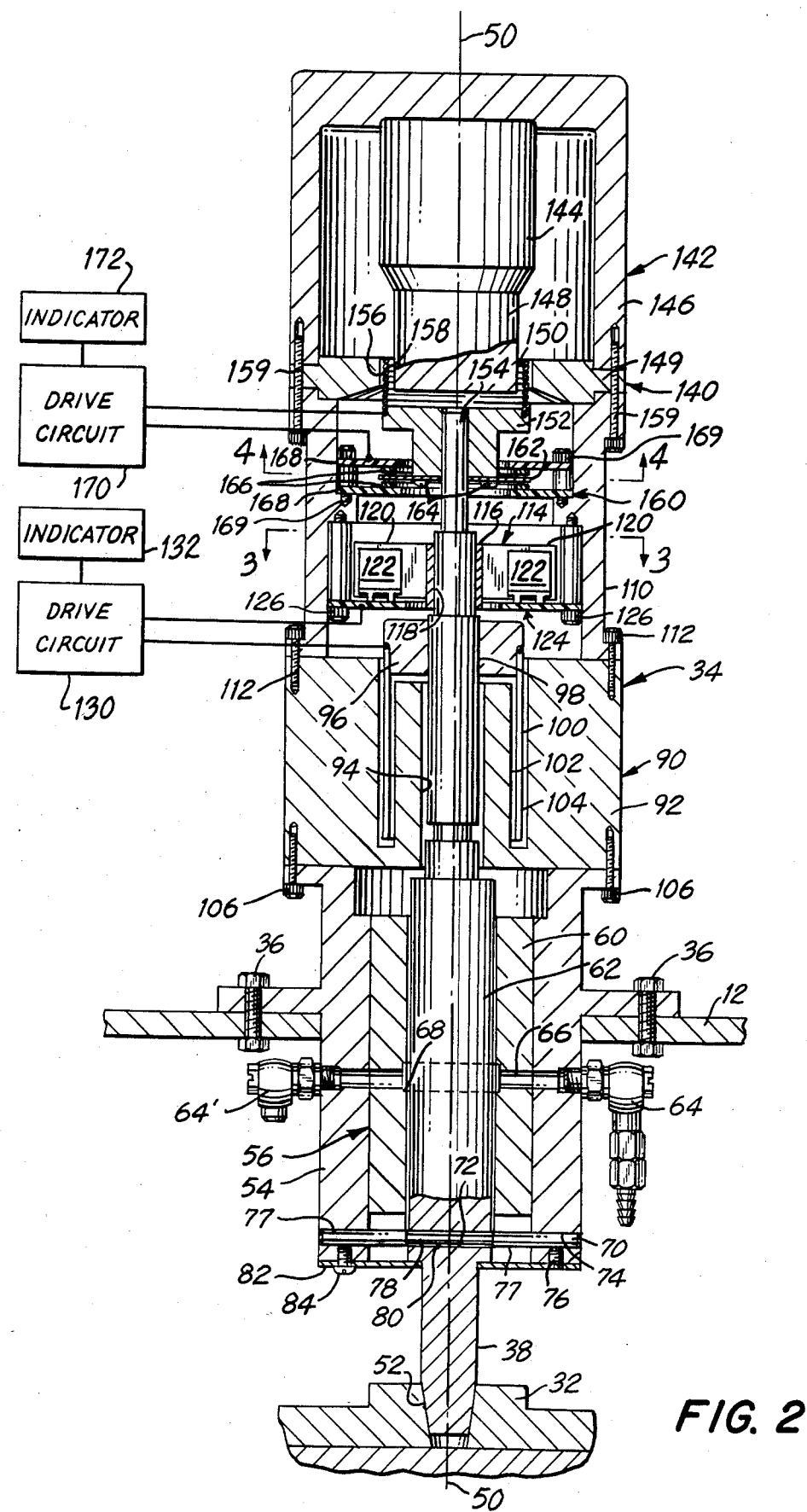
FIG. 2 is a longitudinal cross-sectional view of a portion of the apparatus.

Turning now to FIG. 2, spindle 38 extends axially along a fixed axis 50 passing upwardly through the transducer assembly 34, the lower end 52 of the spindle 38 projecting downwardly to be engaged with upper coupling 32. Transducer assembly 34 includes a lower housing 54 within which there is located a bearing 56 for supporting the spindle 38 for rotational movement about fixed axis 50 and for axial movement along fixed axis 50. In order to reduce to a minimum and essentially eliminate any significant frictional effects of bearing 56 upon free movement of spindle 38, bearing 56 is constructed in the form of an air bearing having a sleeve 60 through which an arbor portion 62 of spindle 38 passes with sufficient clearance to enable the establishment of an appropriate air film between the arbor portion 62 and the sleeve 60. Air under pressure is supplied at an inlet fitting 64 and passes through an air passage 66 to a manifold recess 68 to feed the air film between arbor portion 62 and sleeve 60. Further air inlets may be provided, if necessary, as indicated at second inlet fitting 64'.

Rotational and axial movement of spindle 38 are limited to relatively small displacements by a transverse pin 70 extending through a corresponding opening 72 in the arbor portion 62 of spindle 38. Pin 70 is affixed within a bore 74 in lower housing 54 by means of a set screw 76 which engages one of two end portions 77 of pin 70. Pin 70 has a central portion 78 of reduced diameter so that an annular spacing 80 is provided between the opening 72 and the central portion 78 of pin 70, enabling limited displacement of the spindle 38 in both rotational and axial directions. The position of pin 70 may be shifted selectively by releasing the grip of set screw 76 and sliding an end portion 77 into opening 72 to lock the spindle 38 against all movement relative to lower housing 54, for initial alignment and calibration purposes, as well as for preventing damage during transportation. Alternately, pin 70 may be replaced with an alternate pin of constant diameter (not shown) to immobilize spindle 38 for the same purposes. A lower cover 82 is secured to the lower end of lower housing 54 by screws 84 and closes the lower end against dust and other contaminants.

As set forth above, apparatus 10 is intended to measure both the viscous component and the elastic component of forces within the viscoelastic test speciment 40 during shear conditions. To this end, the specimen 40 is placed between table 20 and platen 30 and is coupled to both the table 20 and the platen 30, as described. The axial distance between the table 20 and the platen 30 is adjusted to precisely the thickness of the test specimen 40 under static conditions, as by relative axial movement between upper support member 14 and lower support member 16 of the frame 12. In this manner, platen 30 is located at a zero or rest position, as seen in FIG. 1. Motor 24 then is activated to rotate drive shaft 28 and table 20, placing test specimen 40 in shear. Continuous rotation of drive shaft 28 by motor 24 at constant speed will result in steady shear. Other modes of testing are available by oscillation or by intermittent movement of drive shaft 28. In the illustrated embodiment, however, motor 24 rotates drive shaft 28, and consequently table 20, at a selected constant speed to attain desired steady shear conditions in test specimen 40. Upon reaching steady shear conditions, the test specimen 40 will exert a torque upon the platen 30 tending to rotate the platen 30 away from the rest position. Additionally, as a result of the above-described "Weissenberg Effect", the test specimen 40 will exert an axially upward force upon the platen 30 tending to move the platen 30 upwardly away from the rest position. These rotational and axial forces are transmitted directly to spindle 38.

With the pin 70 in the position illustrated in FIG. 2, limited rotational displacement and limited axial displacement of spindle 38 are permitted by virtue of annular spacing 80, in response to the rotational and axial forces transmitted to the spindle 38 from the platen 30. Transducer assembly 34 provides a rotational counterforce and an axial counterforce, the counterforces biasing the spindle 38 and the platen 30 toward the rest position. Once the counterforces each reach a magnitude which balances the forces exerted by the test specimen upon the platen 30, and the platen 30 is restored to the rest position, the magnitude of the rotational counterforce provides a measure of the viscous component of the modulus of the material of the test specimen and the magnitude of the axial counterforce provides a measure of the elastic component of the modulus. Hence, the desired forces actually are measured at zero compliance.

Figure 3:
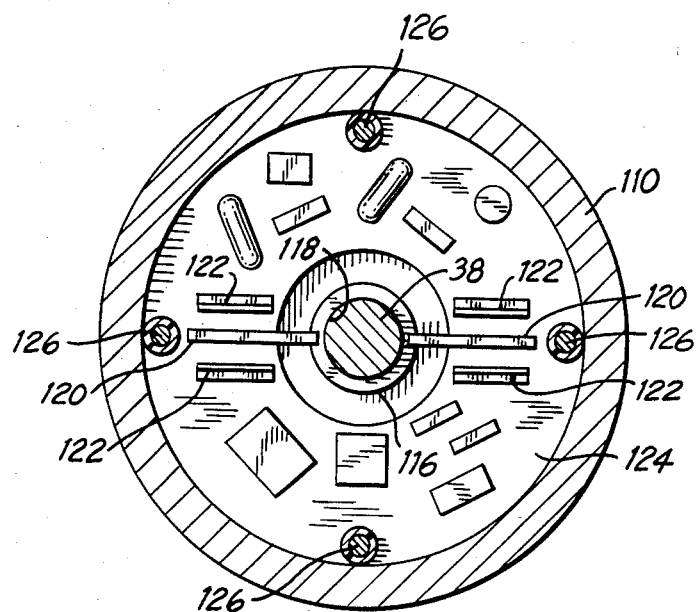
FIG. 3 is a transverse cross-sectional view taken along line 3—3 of FIG. 2.
Figure 4:
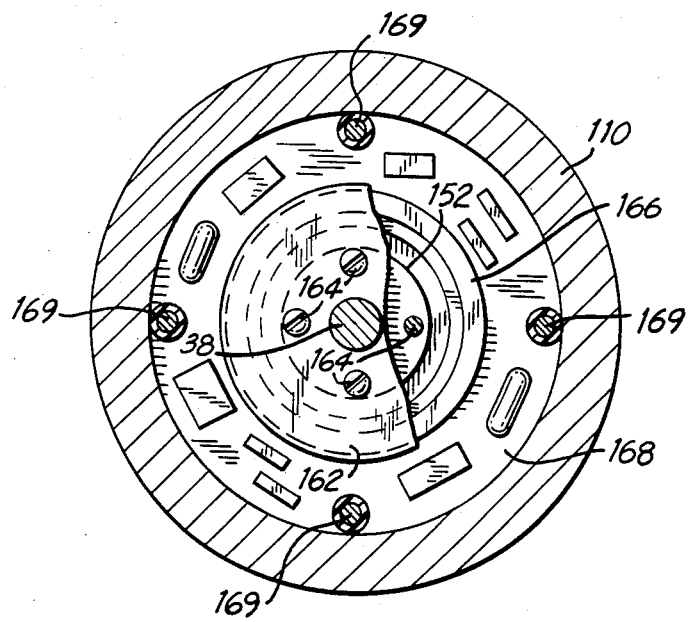
FIG. 4 is a transverse cross-sectional view taken along line 4—4 of FIG. 2.

Referring now to FIGS. 2, 3 and 4, spindle 38 extends upwardly through a first transducer 90. Transducer 90 includes an annular magnet 92, preferably in the form of a permanent magnet, having a central bore 94 through which the spindle 38 passes. A first armature 96 is affixed to the spindle 38 at 98 for movement with the spindle and has a cuplike configuration including a cylindrical extension 100 projecting downwardly into a corresponding annular gap 102 in magnet 92 and carrying a plurality of windings 104 oriented so that upon passing electrical current through the windings 104, the armature 96 will tend to rotate about axis 50 to rotate spindle 38 about axis 50. Magnet 92 is affixed to lower housing 54, as by screws 106, and remains stationary.

A detector housing 110 is secured to the magnet 92, as by screws 112, and houses a first detector 114 for detecting rotational displacement of the spindle 38, and consequently the platen 30, away from the rest position. As best seen in FIG. 3, as well as in FIG. 2, first detector 114 includes a rotor 116 affixed to the spindle 38 at hub 118 and having radially-extending capacitive elements in the form of vanes 120. When the platen 30 and spindle 38 are at the rest position, each of the vanes 120 is centered circumferentially between a pair of parallel capacitive elements in the form of plates 122 mounted upon an annular circuit board 124 secured to the detector housing 110 by screws 126. Each vane 120 and the corresponding pair of plates 122 comprise a variable capacitor so that any rotational movement of spindle 38 will move vanes 120 to effect a change in capacitance discernable by circuitry in the circuit board 124.

A first drive circuit 130 is connected to the first detector 114 and to the first transducer 90 so that the change in capacitance effected by rotational displacement of the platen 30 and spindle 38 away from the rest position will generate current in the windings 104 of armature 96 of transducer 90 to actuate the transducer 90 in response to the first detector 114 to return the spindle 38 and platen 30 rotationally to the rest position and maintain the platen 30 and spindle 38 at the rest position with a rotational counterforce which balances the rotational force exerted by the test specimen 40 upon the platen 30. A first indicator 132 indicates the magnitude of the rotational counterforce required to maintain the balance. Thus, the magnitude of the rotational counterforce is measured at zero compliance.

Spindle 38 extends upwardly still further to pass beyond first detector 114 and into a second transducer 140. Second transducer 140 has a magnet assembly 142 which includes a permanent magnet 144, a magnet housing 146, a first stator 148 and a second stator 149, all establishing an annular gap 150. A second armature 152 is affixed to spindle 38 at the upper end 154 of the spindle and has a cuplike configuration including a cylindrical extension 156 projecting upwardly into the gap 150 of the magnet assembly 142. Cylindrical extension 156 carries a plurality of windings 158 oriented so that upon passing electrical current through the windings 158, the armture 152 will tend to translate axially along axis 50 to move spindle 38 along axis 50. Magnet assembly 142 is affixed to detector housing 110 by screws 159 and remains stationary.

Detector housing 110 houses a second detector 160 for detecting axial displacement of the spindle 38, and consequently the platen 30, away from the rest position. As best seen in FIG. 4, as well as in FIG. 2, second detector 160 includes a capacitive element in the form of a disk 162 secured for movement with the spindle 38 by screws 164 which fasten the disk 162 to armature 152. Disk 162 extends radially outwardly and when the spindle 38 and the platen 30 are at the rest position disk 162 is centered axially between a pair of parallel capacitive elements in the form of rings 166, each mounted upon a corresponding annular circuit board 168 secured to the detector housing 110 by screws 169. The disk 162 and the rings 166 comprise a variable capacitor so that any axial movement of spindle 38 will move disk 162 to effect a change in capacitance discernable by circuitry in the circuit boards 168.

A second drive circuit 170 is connected to the second detector 160 and to the second transducer 140 so that the change in capacitance effected by axial displacement of the platen 30 and spindle 38 away from the rest position will generate current in the windings 158 of armature 152 of transducer 140 in response to the second detector 160 to return the spindle 38 and platen 30 axially to the rest position and maintain the platen 30 and spindle 38 at the rest position with an axial counterforce which balances the axial force exerted by the test specimen 40 upon the platen 30. A second indicator 172 indicates the magnitude of the axial counterforce required to maintain the balance. Thus, the magnitude of the axial counterforce is measured at zero compliance.

When the test speciment 40 is in a state of steady shear and the transducer assembly 34 is maintaining the platen 30 at the rest position, the first indicator 132 provides a measure of the viscous component of forces within the test specimen 40 and the second indictor 172 provides a measure of the elastic component of forces within the test specimen 40, thereby enabling the concurrent measurement of the viscous and elastic components of the modulus of the material being tested. The ability to measure both the viscous and elastic components simultaneously and at zero compliance enables increased accuracy in the results since the conditions under which each component is measured are the same. Moreover, the present apparatus and method increases the ease with which the measurements are made while reducing the time required to obtain the desired data. Further, the ability to measure the magnitude of the counterforces at zero compliance eliminates extraneous effects, such as the effects of temperature variations in the apparatus, and certain mechanical effects resulting from displacements, such as hysteresis effects in forces measured through displacements in a spring.

It is noted that the construction of the first and second transducers 90 and 140 and the corresponding first and second detectors 114 and 160 is such that the transducers and detectors may be operated simultaneously without affecting one another. In other words, the first transducer and its corresponding first detector will operate independent of the operation of the second transducer and its corresponding second detector and provide consistently accurate results regardless of the state of the second transducer and the second detector and vice-versa. Thus, it is apparent that a small axial displacement of the first armature 96 within gap 102 of magnet 92 will not affect the ability of the first transducer 90 to maintain the spindle 38 rotationally at the rest position, while rotational displacement of the second armature 152 within gap 150 of the magnet assembly 142 will not affect the ability of the second transducer 140 to maintain the spindle 38 axially at the rest position. Likewise, axial movement of the vanes 120 between the plates 122 of the first detector 114 will not affect the ability of the first detector 114 to detect rotational movement, and rotational movement of the disk 162 between the rings 166 of the second detector 160 will not affect the ability of the second detector 160 to detect axial displacement of the spindle 38 and the platen 30. Hence, simultaneous operation of the components of the transducer assembly 34 is accomplished and enables the simultaneous measurement of the characteristics being investigated. Although the illustrated detectors 114 and 160 are variable capacitance devices and are preferred because of the advantages offered by the described variable capacitance arrangement, it will become apparent to those skilled in the art that other detectors are available for use in connection with the transducers 90 and 140.

The construction of the transducer assembly enables exceptional accuracy by reducing extraneous influences. Thus, spindle 38 and all of the members mounted on the spindle 38 for movement therewith, such as the armatures 96 and 152, the vanes 120 and the disk 162, all are constructed of non-magnetic materials so as to eliminate any tendency of the spindle 38 to seek a preferred position as a result of the influence of reluctance torque. A preferred material for the spindle 38, the vanes 120 and the disk 162 is aluminum.

It is to be understood that the above detailed description of a preferred embodiment is provided by way of example only. Various details of design and construction may be modified without departing from the true spirit and scope of the invention as set forth in the appended claims.

The embodiments of the invention in which an exclusive property or privilege is claimed are defined as follows:

1. Apparatus for measuring the viscous component and the elastic component of forces within a viscoelastic test specimen placed in shear, the test specimen being coupled to a platen having a rest position, the platen being displaceable from the rest position rotationally and axially relative to a fixed axis in response to rotational and axial forces exerted by the test specimen upon the platen as a result of said viscous component and said elastic component, the apparatus comprising:

a first transducer coupled with the platen for applying a rotational counterforce to the platen for biasing the platen toward the rest position;

a first detector for detecting rotational movement of the platen away from the rest position;

first drive means for actuating the first transducer in response to the first detector to balance the rotational force exerted by the test specimen upon the platen with the rotational counterforce exerted by the first transducer upon the platen and maintain the platen at the rest position;

first indicating means for indicating the magnitude of the rotational counterforce;

a second transducer coupled with the platen for applying an axial counterforce to the platen for biasing the platen toward the rest position;

a second detector for detecting axial movement of the platen away from the rest position;

second drive means for actuating the second transducer in response to the second detector to balance the axial force exerted by the test specimen upon the platen with the axial counterforce exerted by the second transducer upon the platen and maintain the platen at the rest position; and second indicating means for indicating the magnitude of the axial counterforce;

whereby the first indicating means provides a measure of the viscous component of forces within the test specimen and the second indicating means provides a measure of the elastic component of forces within the test specimen when the platen is at the rest position.

2. The invention of claim 1 including a spindle coupled with the platen for rotational movement with the platen about the fixed axis and for axial movement with the platen along the fixed axis, and wherein the first transducer and the second transducer are coupled with the spindle such that the rotational counterforce and the axial counterforce are applied simultaneously upon the platen, and the first and second indicating means simultaneously provide a measure of the viscous component and the elastic component of the forces within the test specimen.

3. The invention of claim 2 wherein the spindle is constructed of a non-magnetic material.

4. The invention of claim 3 wherein the first and second transducers each include at least one movable component part coupled for movement with the spindle and each said movable component part is constructed of non-magnetic materials.

5. The invention of claim 2 wherein the first detector and the second detector both are coupled with the spindle.

6. The invention of claim 5 wherein the spindle is constructed of a non-magnetic material.

7. The invention of claim 6 wherein the first and second detectors each include at least one movable member coupled for movement with the spindle and each said movable member is constructed of non-magnetic materials.

8. The invention of claim 7 wherein the first and second transducers each include at least one movable component part coupled for movement with the spindle and each said movable component part is constructed of non-magnetic materials.

9. The invention of claim 2 wherein at least one of the first detector and the second detector comprises variable capacitance means coupled to the spindle.

10. The invention of claim 9 wherein at least one of the first detector and the second detector includes a first capacitive element and a second capacitive element, the second capacitive element being carried by the spindle for movement relative to the first capacitive element to change the capacitance of the variable capacitance means.

11. The invention of claim 10 including means mounting the second capacitive element of the first detector for rotational movement with the spindle to change the capacitance of the variable capacitance means.

12. The invention of claim 11 wherein the second capacitive element of the first detector is movable with the spindle axially relative to the first capacitive element without a change in the capacitance of the variable capacitance means.

13. The invention of claim 10 including means mounting the second capacitive element of the second detector for axial movement with the spindle to change the capacitance of the variable capacitance means.

14. The invention of claim 13 wherein the second capacitive element of the second detector is movable with the spindle rotationally relative to the first capacitive element without a change in the capacitance of the variable capacitance means.

15. The invention of claim 10 wherein the spindle and the second capacitive element both are constructed of non-magnetic materials.

16. The invention of claim 1 wherein at least one of the first detector and the second detector comprises variable capacitance means responsive to movement of the platen.

17. The invention of claim 16 wherein at least one of the first detector and the second detector includes a first capacitive element and a second capacitive element, the second capacitive element being coupled with the platen for movement relative to the first capacitive element to change the capacitance of the variable capacitance means.

18. The invention of claim 17 including means mounting the second capacitive element of the first detector for rotational movement with the platen to change the capacitance of the variable capacitance means.

19. The invention of claim 18 wherein the second capacitive element of the first detector is movable with the platen axially relative to the first capacitive element without a change in the capacitance of the variable capacitance means.

20. The invention of claim 17 including means mounting the second capacitive element of the second detector for axial movement with the platen to change the capacitance of the variable capacitance means.

21. The invention of claim 20 wherein the second capacitive element of the second detector is movable with the platen rotationally relative to the first capacitive element without a change in the capacitance of the variable capacitance means.

22. The method of measuring the viscous component and the elastic component of forces within a viscoelastic test specimen placed in shear, the test specimen being coupled to a platen having a rest position, the platen being displaceable from the rest position rotationally and axially relative to a fixed axis in response to rotational and axial forces exerted by the test specimen upon the platen as a result of said viscous component and said elastic component, the method comprising the steps of:
applying a rotational counterforce to the platen for biasing the platen toward the rest position;
balancing the rotational force exerted by the test specimen upon the platen with the rotational counterforce applied to the platen to maintain the platen at the rest position;
determining the magnitude of the rotational counterforce necessary to balance the rotational force;
applying an axial counterforce to the platen for biasing the platen toward the rest position;
balancing the axial force exerted by the test specimen upon the platen with the axial counterforce applied to the platen to maintain the platen at the rest position; and
determining the magnitude of the axial counterforce necessary to balance the axial force;
whereby the magnitude of the rotational counterforce provides a measure of the viscous component of forces within the test specimen and the magnitude of the axial counterforce provides a measure of the elastic component of forces within the test specimen when the platen is at the rest position.

23. The invention of claim 22 wherein the rotational counterforce and the axial counterforce are applied simultaneously to the platen, and the magnitudes of the rotational counterforce and the axial counterforce are determined simultaneously.

* * * * *